United States Patent [19]

Haslanger

[11] Patent Number: 4,463,183
[45] Date of Patent: Jul. 31, 1984

[54] METHOD FOR PREPARING A PROSTACYCLIN INTERMEDIATE

[75] Inventor: Martin F. Haslanger, Lambertville, N.J.

[73] Assignee: E. R. Squibb & Sons, Inc., Princeton, N.J.

[21] Appl. No.: 488,488

[22] Filed: Apr. 25, 1983

Related U.S. Application Data

[62] Division of Ser. No. 368,607, Apr. 15, 1982, , which is a division of Ser. No. 308,737, Oct. 5, 1981, Pat. No. 4,341,710, which is a division of Ser. No. 216,598, Dec. 15, 1980, Pat. No. 4,317,906.

[51] Int. Cl.³ .............................................. C07D 307/83
[52] U.S. Cl. .................................................. 549/311
[58] Field of Search ........................................ 549/311

[56] References Cited
U.S. PATENT DOCUMENTS
4,324,730  4/1982  Fried .................................. 549/311

Primary Examiner—Henry R. Jiles
Assistant Examiner—Bernard Dentz
Attorney, Agent, or Firm—Lawrence S. Levinson; Burton Rodney

[57] ABSTRACT

A method is provided for preparing compounds of the formulae

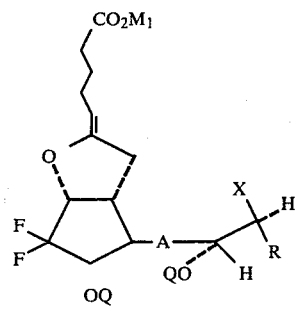

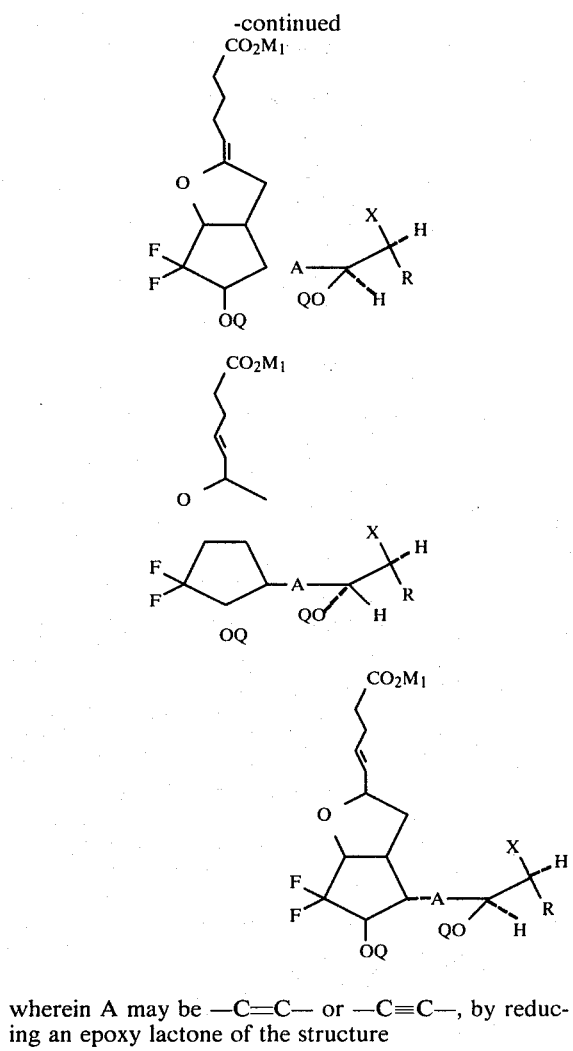

wherein A may be —C=C— or —C≡C—, by reducing an epoxy lactone of the structure

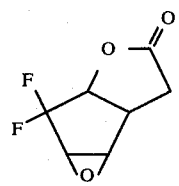

to form the corresponding epoxy hemiacetal, reacting the epoxy hemiacetal with a silyl compound to form an epoxy silyl acetal, reacting the epoxy silyl acetal with an acetylenic derivative to form a silyl acetal, removing the silyl protecting group to form a hemiacetal, reacting the hemiacetal compound with an appropriate Wittig reagent to form a protected difluoro $PGF_{2\alpha}$ type compound, removing the protecting group, reacting the difluoro $PGF_{2\alpha}$ with an iodine compound to form an iodoether and reacting the iodoether with a base to form the desired compounds.

Novel intermediates produced in the above method are also provided.

1 Claim, No Drawings

METHOD FOR PREPARING A PROSTACYCLIN INTERMEDIATE

This is a division of application Ser. No. 368,607, filed Apr. 15, 1982, which is a division of application Ser. No. 308,737, filed Oct. 5, 1981, now U.S. Pat. No. 4,341,710, which is a divisional of application Ser. No. 216,598, filed Dec. 15, 1980, now U.S. Pat. No. 4,317,906.

The present invention relates to a method for the production of pharmacologically active compounds of the formulae:

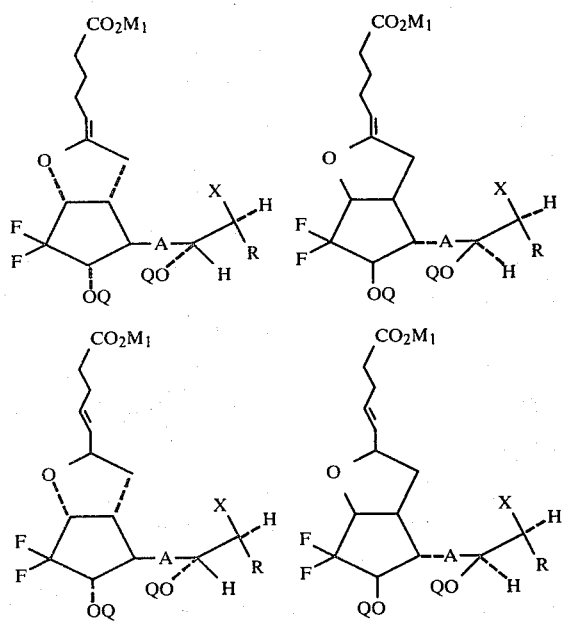

wherein $M_1$ may be H, alkyl, aralkyl or an alkali metal; A may be —C═C— or —C≡C—; X may be H or F; Q is H or acyl; and R may be lower alkyl, lower alkenyl, or aralkyl. Preferably in the practice of this invention M may be H, lower alkyl, a (lower alkyl), for example, benzyl or phenethyl, or an alkali metal, for example, sodium or potassium; A may be —C═C— or —C≡C—; X may be H or F; Q is H; and R may be lower alkyl, for example propyl, butyl or pentyl, lower alkenyl, for example butenyl or pentenyl, or ar (lower alkyl), for example benzyl or phenethyl. Most preferably, M is lower alkyl or sodium; R is lower alkyl of from 3 to 5 carbon atoms; Q is H; A is —C═C— or —C≡C—; and X is H or F.

The term "lower alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substituent, such as F, Br, Cl or I or $CF_3$ or a phenyl substituent.

The term "lower alkenyl" as employed herein includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "aryl" or "Ar" as employed herein refers to monocyclic or bicyclic aromatic groups containing from 6 to 10 carbons in the ring portion, such as phenyl, naphthyl, tetraindiol, substituted phenyl or substituted naphthyl wherein the substituent on either the phenyl or naphthyl may be lower alkyl, halogen (Cl, Br or F), or lower alkoxy (that is, lower alkyl-O).

The term "lower alkoxy" refers to any of the above lower alkyl groups attached to an oxygen (lower alkyl-O).

The term "acyl" as employed herein refers to "lower alkanoyl" groups, that is, any of the above lower alkyl groups attached to a carbonyl group

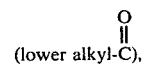

(lower alkyl-C), as well as monocyclic aroyl groups, that is, phenyl, linked to a carbonyl group, the phenyl being unsubstituted or substituted with one, two or three lower alkyl groups, halogen, hydroxy, amino or nitro.

The compounds prepared by the method of this invention are physiologically active compounds which possess prostacyclin-like activity and thus, may be employed for the purpose of lowering elevated blood pressure and of increasing peripheral blood flow. Therefore, such compounds may be employed in the treatment of hypertension or for the relief of circulatory problems.

In addition, the compounds produced by the method of this invention prevent the aggregation of blood platelets thereby removing one of the contributory factors to the formation of atheroschlerotic plaques. As a result, such compounds may be employed in hemodialysis and during open heart surgery where it is important to prevent aggregation of platelets thereby impeding the flow of blood through the filter pads.

In addition, some of the compounds produced by the method of this invention cause regression of the corpus luteum, and they can therefore be used for estrus synchronization in farm animals so as to achieve greater economy in the practice of artificial insemination, or as contraceptive agents in the human female. Being protected from metabolic inactivation these compounds can be administered perorally or intravenously, in contrast to the corresponding natural prostaglandins.

Some of the compounds produced by the method of this invention have also been found to be resistant to the action of the major prostaglandin inactivating enzyme, 15-hydroxyprostaglandin dehydrogenase. Such failure to be destroyed in the body has the effect of prolonging or enhancing the action of these substances when compared with the naturally occurring prostagladins.

Perhaps one of the most important properties of the compounds produced by the method of this invention is the considerable chemical stability which is imparted to them by the presence of the two fluorine atoms in the 10-position. As a result of this greatly increased chemical stability, such compounds retain their biological activity considerably longer than is the case with the naturally occurring prostacyclins.

The pharmacologically active compounds produced by the method of this invention may be administered to animal or patient being treated therewith in any manner known and convenient to the skilled worker practicing the invention, the dosage and concentration of the final product being adjusted to the requirement of the patient and the properties of the respective compound being employed. The skilled worker may prepare the final products in such compositions and dosage forms as are usually employed for such purposes, depending upon the route of administration selected for the ultimate composition, for example, parenteral, peroral or topical final dosage and routes of administration.
The process of this invention entails a number of steps generally represented by the following reaction sequence.
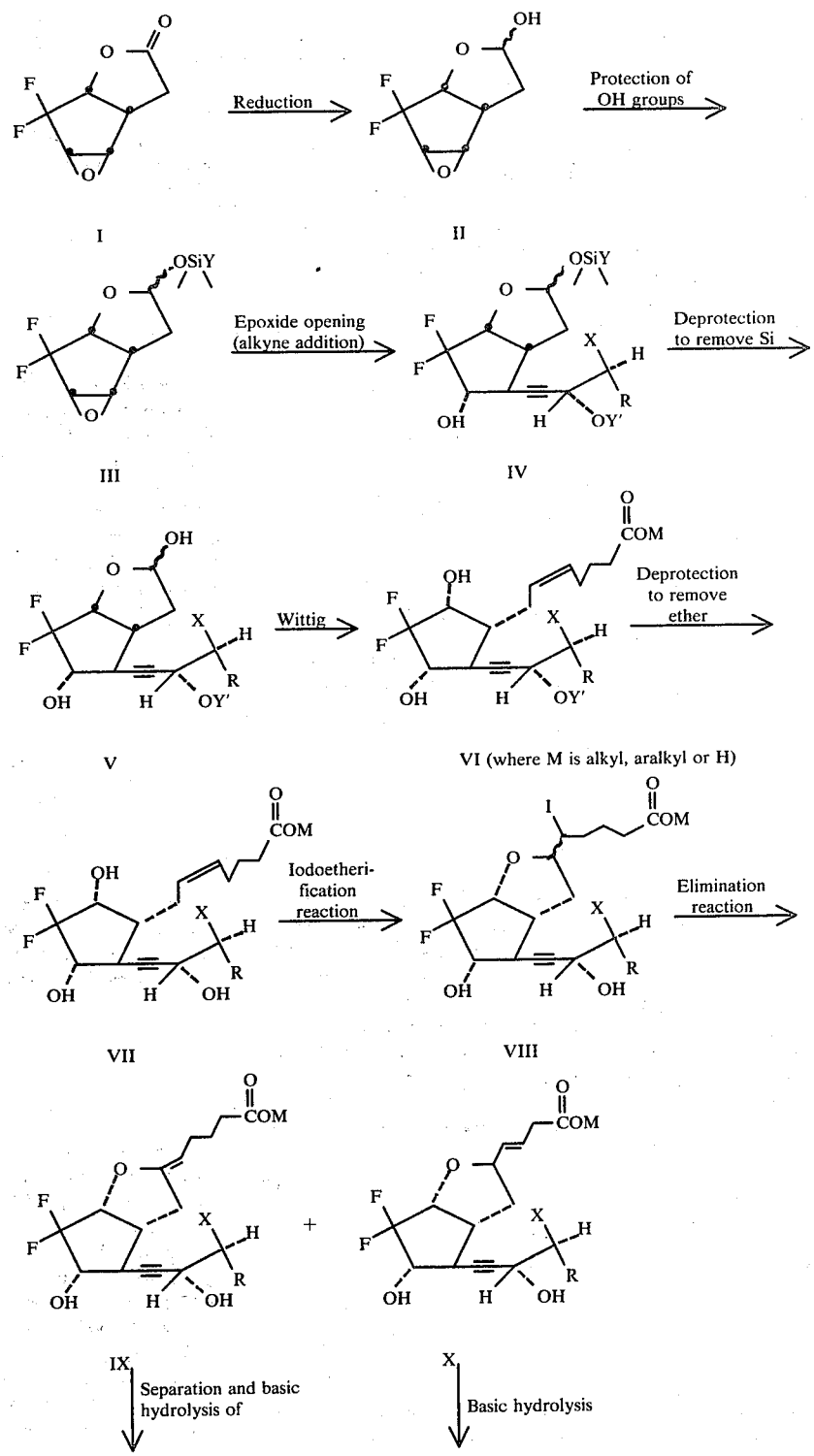

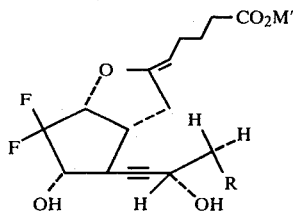 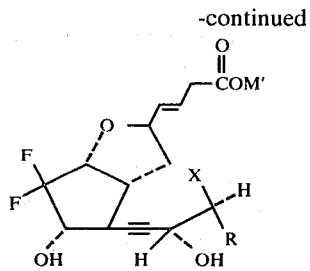

XI where M' may be an
alkali metal
(Difluoro, dehydro PGI₂)

XIA
($\Delta^4$ isomer of Difluoro, dehydro PGI₂)

In carrying out the process of the present invention as outlined in the above reaction sequence, the difluoroepoxy lactone I is reduced with a hydride reducing agent, such as diisobutylaluminum hydride, at low temperature, for example, within the range of from about $-100°$ to about $-40°$ C. in the presence of an inert hydrocarbon solvent, such as an aromatic solvent examples of which include toluene, or xylene, to form the difluoro epoxy hemiacetal II

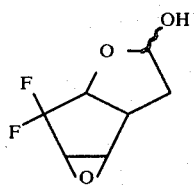   II which is a new intermediate in accordance with the present invention.

The new difluoro epoxy hemiacetal II is then reacted with a silyl protecting compound preferably having the structure

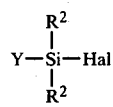   A wherein $R^2$ is lower alkyl or aryl, Y is an ether protecting group and can be lower alkyl or aryl, preferably t-butyl, and Hal is Cl or Br, such as t-butyl dimethylsilyl chloride, employing a molar aratio of II:A of within the range of from about 0.9:1 to about 0.3:1, in the presence of an inert solvent, such as dimethylformamide, acetonitrile or dimethylacetamide and an organic base, such as triethylamine and 4-(N,N-dimethylamino)pyridine, to form the silyl acetal III which is also a new intermediate in accordance with the present invention

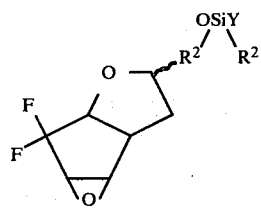   III wherein Y is an ether protecting group, for example, lower alkyl, such as t-butyl.

The silyl acetal III is subjected to an epoxy opening or alkyne addition reaction by reacting the silyl acetal III with a dialkyl alkynyl aluminum derivative B $$\begin{array}{c} R^3 \\ \diagdown \\ AlC\equiv C \\ \diagup \\ R^3 \end{array} \begin{array}{c} X \quad H \\ \diagdown \diagup \\ \diagup \diagdown \\ H \quad OY' \end{array} R \qquad B$$

wherein $R^3$ is lower alkyl, preferably methyl or ethyl, Y' is an alcohol protecting group, for example, lower alkyl, such as t-butyl, and X and R are as defined hereinbefore, employing a molar ratio of III:B of within the range of from about 1:1 to about 0.5:1, in the presence of an aromatic solvent, such as toluene, benzene or xylene, at a temperature of within the range of from about 40° to about 80° C., to form the silyl acetal IV which is also a new intermediate in accordance with the present invention

IV

The novel silyl acetal IV is treated with a mineral acid, such as hydrofluoric acid to form the hemiacetal V which is subjected to a Wittig reaction by reacting same with a triphenylphosphonioalkanoic acid of the structure $$(C_6H_5)_3P=T C(CH_2)_n CO_2 M \qquad \text{with } W, W \text{ on } T \qquad C$$

wherein T is CH or CF, W is H or F, M is H, aralkyl or lower alkyl, and n is 1 or 2, in a molar ratio of V:C of within the range of from about 0.3:1 to about 0.1:1, in the presence of an inert solvent, such as dimethyl sulfoxide, tetrahydrofuran or glyme, and the crude prostaglandin so-formed is treated with a diazoalkane, such as $CH_2N_2$, to form the 10,10-difluoro-13-dehydroprostaglandin VI (difluoro, dehydro PGF₂α ether).

The difluoro, dehydro PGF₂α ether VI is treated to remove the Y' protecting group by reacting VI with a strong acid, for example, trifluoroacetic acid, sulfuric acid, and the like in the presence of an inert solvent, such as anisole, to form the 10,10-difluoro-1,3-dehydro-prostaglandin VII which is cyclized by an iodoetherification reaction by treatment with excess halogen or halogenimide, such as iodine in the presence of a solvent, such as methylene chloride and weak base, such as sodium bicarbonate or potassium bicarbonate employing a molar ratio of VII:halogen or from about 1:1 to about 0.2:1, to form the iodoether VIII.

Treatment of the iodoether VIII with a base, such as diazabicyclo[5,4,0]undec-5-ene results in the formation of the prostacyclin IX and its Δ⁴-isomer X in the form of their esters which comprise physiologically active end products. Additional physiologically active products are obtained by hydrolysis of the esters with, for example, sodium hydroxide, to form the corresponding salts XI and the salts XIA of the Δ⁴-isomer X.

The enantiomer of the afore-described difluoro, dehydro PGI$_2$, that is

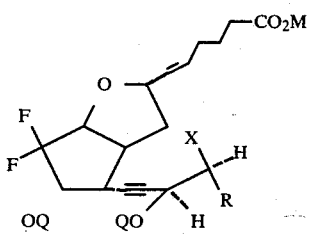   XI' and its Δ⁴ isomer (or the enantiomer of the Δ⁴ isomer of difluoro, dehydro PGI$_2$)

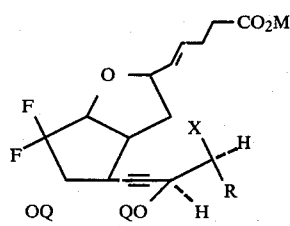   XIA' may be prepared by reacting the epoxy silyl acetal III with a dialkyl alkynyl aluminum derivative B'

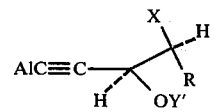   B' to form the silyl acetal

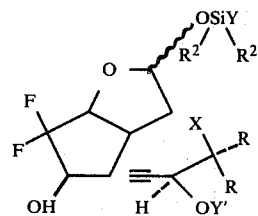   IV' which is then treated as per steps IV to IX (including X to XA) to form the enantiomers XI' and XIA'.

The 10,10-difluoroprostaglandins and the 10,10-difluoroprostacyclins possessing a trans double bond in place of the acetylenic bond present in the compounds heretofore described may be prepared as follows. The synthesis of these compounds starts with the protected ether IV (or the corresponding enantiomer IV') whose triple bond may be reduced with, for example, lithium aluminum hydride to form the allylic alcohol IVA or its corresponding enantiomer IVA' which is a new intermediate in accordance with the present invention.

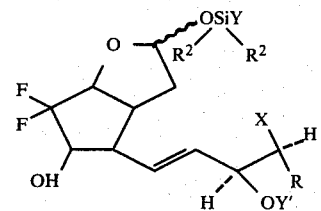   IVA'

Compound IVA or IVA' may now be treated in the manner hereinbefore described for the sequence of compounds IV to XI (XIA), the conditions being very similar to those outlined for the above series of reactions. In this manner there result these additional final pharmacologically active products XIB and XIC.

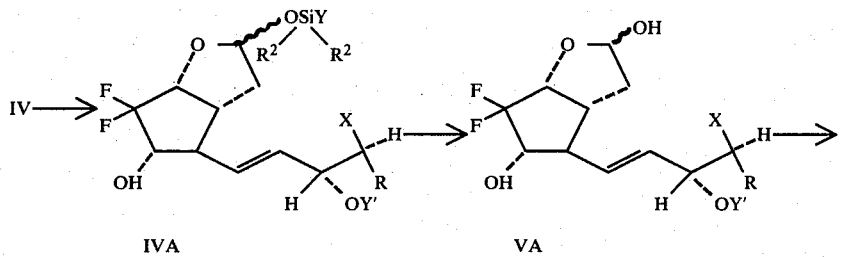

IVA      VA

-continued
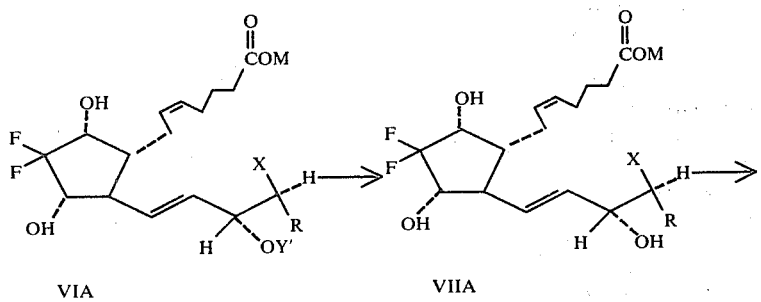
VIA    VIIA
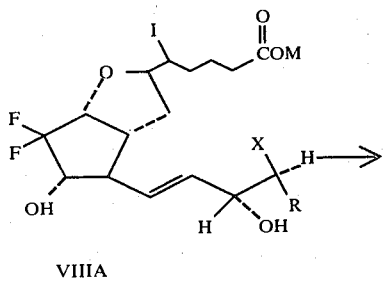
VIIIA
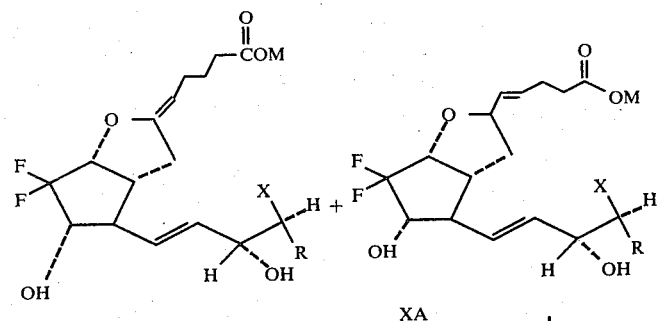
IXA    XA
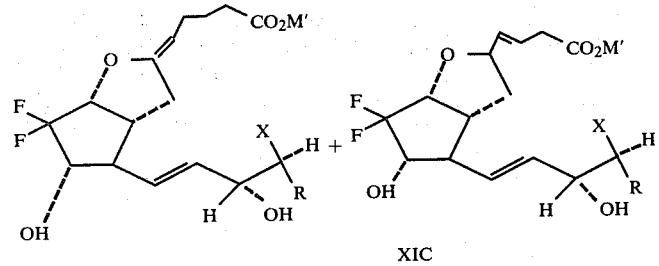
XIB    XIC
The starting difluoro epoxy lactone I may be prepared by the following process as outlined by the sequence of reactions set out below.
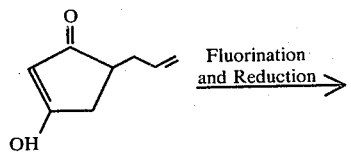
XII
-continued
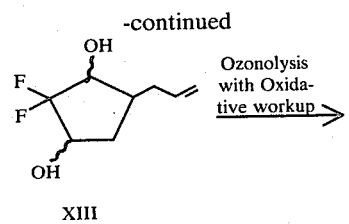
XIII

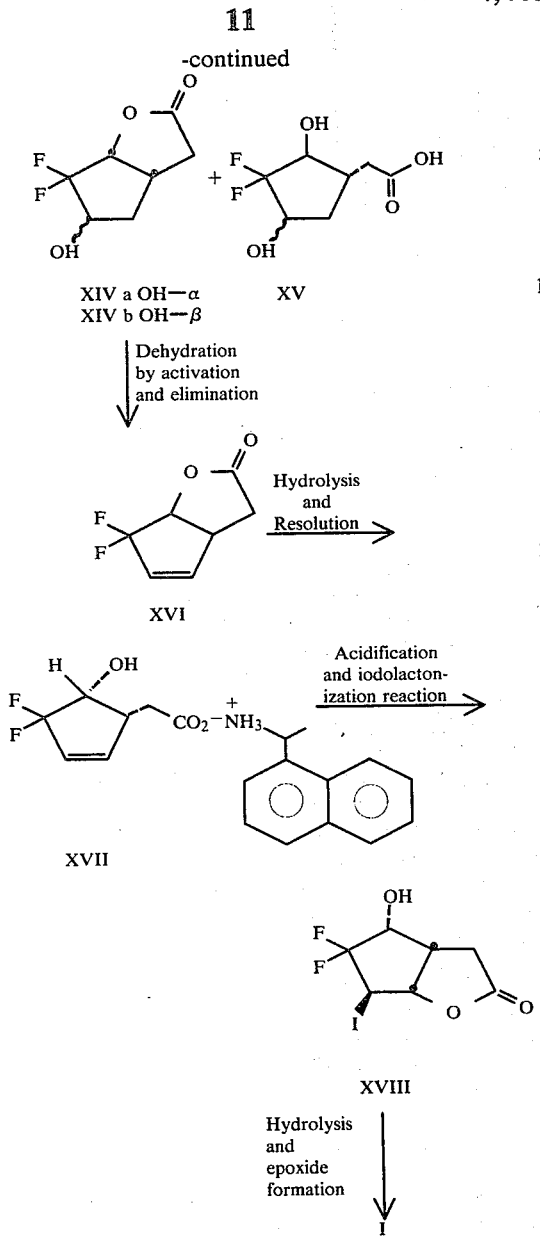

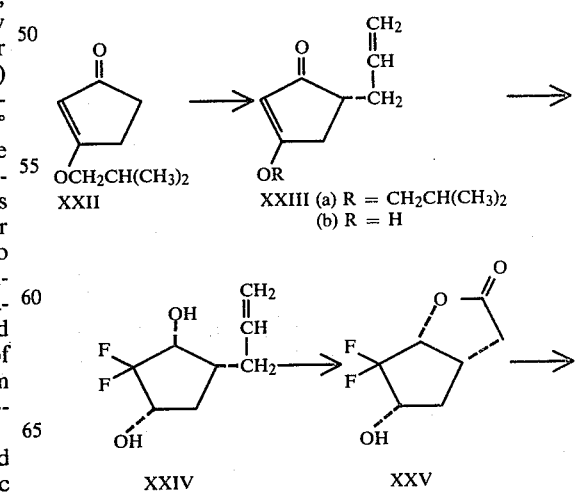

potassium bicarbonate and ethyl acetate, and are subjected to dehydration by activation and elimination, for example, by reaction with trifluoromethanesulfonic anhydride (molar ratio of XIV:anhydride of from about 1:1 to about 0.5:1) in pyridine resulting in the unsaturated lactone XVI.

At this stage it becomes optional to proceed either with the racemic compound XVI or to resolve XVI into its optical antipodes. Whichever course is followed, the reactions themselves and the precise conditions under which they are performed are identical for the whole sequence until the final products are obtained.

The resolution of the lactone XVI involves hydrolysis of the latter with a base, such as potassium or sodium hydroxide, by the reaction of the resultant salt with optically active α-(1-naphthyl)-ethylamine yielding crystalline salts which are recrystallized to constant specific rotation and then treated with a base to decompose the salts and to remove the α-(1-naphthyl)ethylamine by extraction with ether. The resultant salt XVII is then directly converted into the iodo lactone XVIII by treatment with iodine and dilute KOH or NaOH employing a molar ratio of XVII:$I_2$ of from about 1:1 to about 0.5:1.

The resultant iodo lactone XVIII may then be carried forward by the process of this invention either in optically active form or as the racemate. The iodo lactone XVIII is then converted into the epoxy lactone starting material I by treatment with base followed by mild acid treatment. The epoxy lactone I may then be used to form the difluoro, dehydro $PGI_2$, and the $\Delta^4$ isomer of difluoro, dehydro $PGI_2$, or the enantiomer of difluoro, dehydro $PGI_2$ and the enantiomer of the $\Delta^4$ isomer of the difluoro, dehydro $PGI_2$ or to form the corresponding difluoro PGI compounds.

Alternatively, the starting difluoro epoxy lactone I may be prepared as described by Fried et al, "10,10-Difluoro-1,3-dehydroprostacyclin: A Chemically and Metabolically Stabilized Potent Prostacyclin", *J. Med. Chem.* 1980, 23, 234–237, according to the following reaction sequence.

In carrying out the above process for preparing the difluoro epoxy lactone starting material of formula I, the 5-allyl-cyclopentan-1,3-dione XII is fluorinated by reaction with, for example, perchloryl fluoride (molar ratio of XII:fluoride of from about 0.5:1 to about 0.1:1) in the presence of a weak base, such as sodium or potassium bicarbonate, at a temperature of from about −10° to about 30° C.; the intermediate difluoro derivative resulting from this reaction is not isolated but is immediately reduced with a hydride reducing agent, such as sodium borohydride or lithium borohydride (molar ratio of difluoro compound:hydride of from about 1:1 to about 0.2:1) to form the difluoro diol XIII. The compound is subjected to ozonolysis followed by an oxidative work-up, for example, by heating with formic acid and, for example, hydrogen peroxide, (molar ratio of XIII:peroxide of from about 1:1 to about 0.3:1) to form the isomeric lactones XIVa and XIVb and the 3,3-difluoro-2,4-dihydroxycyclopentaneacetic acid XV.

The isomeric lactones XIVa and XIVb are separated from the 3,3-difluoro-2,4-dihydroxycyclopentaneacetic acid XV, for example, by extraction with, for example,

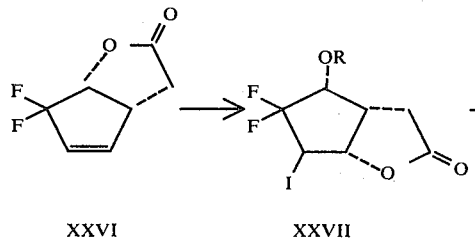

XXVI  XXVII

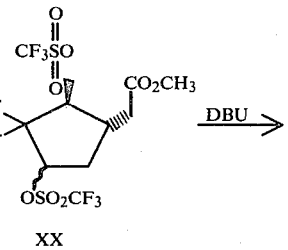

XX

In carrying out the above method for making the difluoro epoxy lactone I, the isobutyl enol ether XXII of cyclopentane-1,3-dione (i-BuOH, benzene, p-toluenesulfonic acid), is alkylated (lithium diisopropylamide, allyl iodide at −80° C. in THF) to form XXIIIa. Hydrolysis (1N HCl at 50° C., 2 h) affords the parent dione XXIIIb which solidifies on standing. Difluorination is accomplished by bubbling FClO₃ through a solution of XXIIIb in methanol containing 2 equivalents of KHCO₃ at 20° C. until neutral. The resulting difluoro diketone is reduced directly with potassium tri-sec-butylborohydride in THF, after addition of toluene and careful removal of methanol in vacuo, to yield, after chromatography on silica gel, the all-cis-diol XXIV and a mixture of XXV and the trans-diol. Ozonolysis of XXV in methanol at −70° C. [workup with (CH₃)₂S] produces the anomeric hemiacetals which solidifies spontaneously, and are immediately oxidized to the lactone XXV with KI₃ in aqueous sodium carbonate at 25° C. Dehydration of XXV or its β isomer proceeds via the triflate (trifluoromethylsulfonic anhydride/pyridine, −10° C.→+10° C., 1.5 h, then 120° C. for 45 minutes), affording after chromatography the olefin XXVI, m.p. 36°–37° C. The olefinic lactone XXVI is saponified (0.5N KOH in MeOH, 20° C., 18 h) and iodolactonized [dry ice to pH 9, I₂ (10 equivalents), 25° C., 18 h] to form XXVII. Base treatment of XXVII (1N KOH in MeOH, 25° C., 24 h) followed by acidification effects only partial lactonization of the intermediate epoxy acid, which is completed by methylation with CH₂N₂ and allowing the methyl ester to remain on a silica gel column for 24 h prior to elution: yield of I, m.p. 92°–92.5° C.

The intermediate compounds of formula XVI may also be prepared from the intermediate of formula XV in accordance with the following sequence of reactions

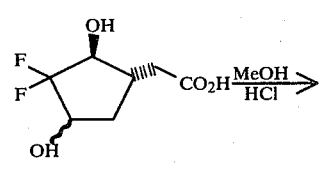

XV

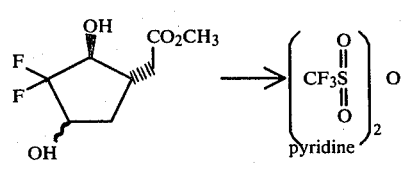

XIX

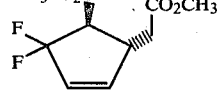

XXI  XVI

In carrying out the above process for preparing compounds XVI, the 3,3-difluoro-2,4-dihydroxy-cyclopentaneacetic acid XV (obtained from acidification of potassium bicarbonate extract from the ozonolysis reaction mixture, described hereinbefore in the preparation of compounds XIV) is reacted with methanolic hydrochloric acid to form the methyl ester XIX which is dehydrated by activation and elimination, for example, by reaction with trifluoromethanesulfonic anhydride in pyridine to form the triflate XX. The triflate XX is then reacted with a base, such as diazabicyclo[5,4,0]undec-5-ene in a molar ratio of XX:DBU of from about 1:1 to about 0.1:1 to form the olefin ester XXI which is treated with base, such as potassium hydroxide, acidified and then reacted with trifluoroacetic anhydride (molar ratio of XXI:anhydride of from about 1:1 to about 0.5:1) to form the difluoro lactone XVI.

It should be understood in the practice of this invention that in the preparation of the various compounds producible thereby, whenever a compound having free hydroxy groups is produced it may be further treated in accordance with methods well known in the art to provide the respective acyl derivatives thereof. Thus, a compound prepared by the method of this invention having free hydroxy groups may be treated with a suitable acylating agent, such as those derived from hydrocarbon carboxylic acids of twelve carbon atoms or less to yield the desired acyloxy derivatives as is well known to the skilled worker.

In addition to the foregoing description, it should be understood that the procedures and practices employed in the instant invention are equally applicable to the treatment and processing of other and further intermediate and starting materials to yield further final products. For example, for the many substituents, intermediates or even starting materials which may be available to and employable by the skilled worker in the practice, attention is directed to the following U.S. Patents, the disclosures of which are incorporated herein by reference: U.S. Pat. Nos. 4,124,599; 4,158,667; 4,174,441; 4,191,824; 4,198,230; 4,198,500; 4,202,970; 4,202,971 and 4,202,972.

Whenever in this specification and the claims appended thereto a wavy line ( $\{$ ) is employed in the linkage of substituents in the chemical structures set forth, it is meant to denote that the appended moiety may be either in the alpha- or beta-stereochemical configuration in the molecule.

The invention may be further illustrated by the following examples.

EXAMPLE 1

[3aR-[2Z,3aα,4α(5S*),5β,6aα]]-[6,6-Difluorohexahydro-5-hydroxy-4-(3-hydroxy-1-octynyl)-2H-cyclopenta[b]furan-2-ylidene]pentanoic acid (or (8R,9R,11S,12S,15S)-10,10-Difluoro-13-dehydro-prostacyclin methyl ester)

A. 3-Allyl-1,1-difluoro-2,5-dihydroxycyclopentane

A stream of $FClO_3$, purified by bubbling successively through solutions of 2N NaOH and 5% $Na_2S_3O_3$, is bubbled via a gas dispersion tube into a mixture of 2.5 g (18 mmole) 5-allyl-cyclopentan-1,3-dione, and 3.8 g (38 mmole) of finely powdered $KHCO_3$ in 100 ml of ethanol. The temperature of the reaction medium is kept at 10°-25° with an ice bath. The reaction is vented through a water bubbler. Upon disappearance of starting diketone by TLC, flow of $FClO_3$ is stopped and the solution is purged of $FClO_3$ with $N_2$. A solution of KOH in 95% ethanol is used to detect presence of $FClO_3$ in effluent from the reaction flask. The reaction mixture is then cooled to −20° with dry ice/$CCl_4$ and 0.7 g (18 mmole) of $NaBH_4$ is added in three portions. Temperature of the reaction medium is kept below −15° C. After completion of addition, the reaction mixture is stirred at −20° for ½ hour then quenched with solid $NH_4Cl$. The ethanol is removed on a rotary evaporator and the residue is digested with ethyl acetate. The combined ethyl acetate solutions are washed with saturated NaCl and dried ($MgSO_4$). The solvent is evaporated to give a quantitative yield of crude 3-allyl-1,1-difluoro-2,5-dihydroxycyclopentane as a mixture of all possible isomers. A sample of the all cis isomer is obtained by chromatography and characterized spectroscopically. $R_f$=0.45 [silica, benzene/EtOAc (2:1)].

B. 3,3-Difluoro-2,4-dihydroxycyclopentane-1-acetic acid 2,2' lactone

A stream of ozone is passed into a solution of 5 g of the isomeric mixture of 3-allyl-1,1-difluoro-2,5-dihydroxycyclopentane in 300 ml of methanol at −78° until ozone is detected in the effluent stream (aqueous KI solution). The excess ozone is blown out of the reaction mixture with nitrogen, the reaction mixture warmed to ambient temperature and the solvent is evaporated to yield crude product. The crude ozonolysis product is dissolved in 25 ml of 88% $HCO_2H$ and ca. 6.5 ml of 30% $H_2O_2$ is added. The reaction mixture is gently heated (ca. 40°-70°) until a vigorous exotherm occurs. After the exotherm ceases, an additional 13 ml of 30% $H_2O_2$ is added and the reaction is heated at 70° for 10 hours. The solvent is evaporated, the residue is taken up in EtOAc, washed with saturated $KHCO_3$, saturated NaCl and dried ($MgSO_4$). The solvent is evaporated to yield ca. 1.8 g of 3,3-difluoro-2,4-dihydroxycyclopentane-1-acetic acid 2,2' lactone (40% yield from 5-allyl-cyclopentan-1,3-dione). The lactone is a mixture of hydroxyl epimers; the all cis isomer predominates 6:1. The dihydroxy acid is obtained by acidification of the $KHCO_3$ solution and extraction with ethyl acetate. The isomeric lactones are separated by chromatography and characterized spectroscopically.

C. 3,3-Difluoro-1,2-cis-2-hydroxycyclopent-4-ene-1-acetic acid 2,2' lactone

To a solution of 2.3 g (12.9 mmole) crude 3,3-difluoro-2,4-dihydroxycyclopentane-1-acetic acid 2,2' lactone (in 2 ml of pyridine and 120 ml $CH_2Cl_2$) cooled to −20° is added dropwise a solution of 3.81 g (13.5 mmole) of trifluoromethanesulfonic anhydride in 10 ml of $CH_2Cl_2$. Upon completion of addition, reaction is allowed to warm to ambient temperature and stir for ½ hour. The reaction mixture is diluted with $Et_2O$ and pyridinium triflate is filtered off. The filtrate is washed with water, saturated NaCl and dried ($MgSO_4$). Solvent is evaporated to yield 3.4 g of brown solid. To an ice cooled solution of the crude triflate in ca. 100 ml of toluene is added 1.7 g (11 mmole) of 1,5-diaza[5,4,0-]bicycloundec-5-ene (DBU). The reaction mixture is heated at 40°-50° (oil bath temperature) for ½ hour. The cooled reaction mixture is poured into ice/ethyl acetate and the layers are separated. The ethyl acetate phase is washed with pH 5.5 acetate buffer, saturated NaCl and dried ($MgSO_4$). The solution is filtered through celite and evaporated to yield 1.1 g (72%) of 3,3-difluoro-1,2-cis-2-hydroxycyclopent-4-ene-1-acetic acid 2,2' lactone.

D. (1R,2R) 3,3-Difluoro-2-hydroxy-cyclopent-4-ene-1-acetic acid naphthylethylamine salt To a solution of 6.5 g (0.041 mole) of olefin lactone produced in Part C in 120 ml THF and 85 ml water is added 62 ml of 1N NaOH. The resulting solution is stirred at ambient temperature for 4 hours. The THF is stripped off on a rotary evaporator and ethyl acetate (100 ml) is added. The reaction mixture is acidified with saturated oxalic acid to pH 2. The layers are separated and the aqueous phase is reextracted (4x). The combined ethyl acetate extracts are washed with saturated NaCl and dried ($MgSO_4$). The drying agent is filtered off, the ethyl acetate solution is treated with 8 ml (8.48 g, 0.05 mole) of (R)(+)-1-naphthyl-1-ethylamine and allowed to stand overnight. The salt is collected, dissolved in 2 l. hot ethyl acetate and filtered through celite to remove oxalate salt. The solution is concentrated and crude salt is recrystallized from ethyl acetate (twice) to yield 4.9 g of (1R,2R) 3,3-difluoro-2-hydroxy-cyclopent-4-ene-1-acetic acid naphthylethylamine salt, m.p. 162°-163° C.; $[\alpha]_D$ ($CH_3OH$)= −44.1° (c-1.5).

E. (1S,2S,3R,5R) 4,4-Difluoro-2,5-dihydroxy-3-iodocyclopentane-1-acetic acid 2,2' lactone To an ice cooled suspension of 0.91 g (2.6 mmole) of chiral salt produced in Part D in 200 ml ether is added dropwise 2.65 ml of 1N aqueous methanesulfonic acid. Upon completion of addition, sufficient solid $(NH_4)_2SO_4$ is added to consume the aqueous phase. The ether is decanted and the solids are washed with ether. The combined ethyl ether solutions are dried ($Na_2SO_4$) and evaporated to give a quantitative yield of chiral hydroxy acid as a viscous oil. The hydroxy acid is taken up in 35 ml of 0.1N KOH in methanol and the pH of the solution adjusted to ca. 8.5 with $CO_2$ and $KHCO_3$. To the solution of hydroxy-carboxylate is added 6.7 g (26 mmole) of $I_2$ and the resulting solution allowed to stir at ambient temperature in the dark for 40 hours. Excess $I_2$ is reduced with aqueous $Na_2S_2O_3$ and the solvent is evaporated to give a yellow residue. The residue is digested with ethyl acetate and the combined solutions are washed with saturated Na₂SO₃, saturated NaCl and dried (MgSO₄). Solvent is evaporated to give a quantitative yield of the (1S,2S,3R,5R) 4,4-difluoro-2,5-dihydroxy-3-iodocyclopentane-1-acetic acid 2,2' lactone.

F. (1R,2R,4S,5S) 3,3-Difluoro-2-hydroxy-3,4-epoxycyclopentane-1-acetic acid 2,2' lactone To a solution of 0.75 g (2.5 mmole) iodolactone produced in Part E in 8 ml THF is added 12 ml of 0.42N KOH. The reaction is stirred at ambient temperature for 3½ hours. At the end of this period TLC shows absence of starting lactone. The reaction mixture is acidified with $CO_2$ to pH 7, then to pH 3 with saturated oxalic acid solution. The THF is evaporated and the aqueous solution is saturated with NaCl and extracted with ethyl acetate (4x). Combined ethyl acetate solutions are dried (Na₂SO₄) and the solvent is evaporated to yield 430 mg of crude crystalline epoxy acid. The acid is dispersed in 5 ml $CH_2Cl_2$, cooled with an ice bath and treated dropwise with 0.35 ml (2.5 mmole) of trifluoroacetic anhydride. Upon stirring briefly the acid dissolves and the volatile components are evaporated to yield 410 mg of the (1R,2R,4S,5S) 3,3-difluoro-2-hydroxy-3,4-epoxycyclopentane-1-acetic acid 2,2'-lactone (88% yield from iodolactone of Part E).

G. (1R,2R,4S,5S) 3,3-Difluoro-2-hydroxy-4,5-epoxycyclopentane-1-acetaldehyde 2,2' lactol To a suspension of 403 mg (2.28 mmole) of epoxy lactone produced in Part F in 10 ml of toluene at −78° is added dropwise 14 ml of a 1.5M solution of diisobutylaluminum hydride in toluene. Reaction is allowed to stir at −78° until all of the starting lactone is dissolved (~3-4 hours). The reaction is quenched with 1 equivalent of acetic acid in ether and the dry ice bath is removed. The aluminum complex is quenched with 3N HCl, saturated with NaCl. The reaction mixture is diluted with ethyl acetate and the phases separated. The aqueous phase is extracted with ethyl acetate (4x). The combined organic phase is washed with saturated KHCO₃, saturated NaCl and dried (MgSO₄). The solvent is evaporated to yield 385 mg of the (1R,2R,4S,5S) 3,3-difluoro-2-hydroxy-4,5-epoxycyclopentane-1-acetaldehyde 2,2' lactol.

H. (1R,2R,4S,5S) 3,3-Difluoro-2-hydroxy-4,5-epoxycyclopentane-1-acetaldehyde 2,2' lactol t-butyldimethylsilyl ether To a solution of 384 mg (2.16 mmole) of hemiacetal of part G and 375 mg (2.5 mmole) of tert-butyl dimethylsilyl chloride in 7 ml of DMF is added 303 mg of triethylamine and 60 mg (½ mmole) of 4-(N,N-dimethylamino)pyridine. The resulting solution is stirred at ambient temperature overnight. The reaction is poured into ether/water and the layers are separated. The ether phase is washed with saturated KHCO₃, saturated NaCl and dried (MgSO₄). Solvent is evaporated to yield (1R,2R,4S,5S) 3,3-difluoro-2-hydroxy-4,5-epoxycyclopentane-1-acetaldehyde 2,2'-lactol t-butyldimethylsilyl ether. The crude product is chromatographed on silica with hexane/ethyl acetate to yield 390 mg of the silyl acetal.

I. (8R,9R,11S,12S,15S)-1,2,3,4,5-Pentanor-9,11,15-trihydroxy-10,10-difluoro-13-prostyn-6-al 6,9-lactol, 6-t-butyldimethyl silyl ether, 15-t-butyl ether To a solution of 1 mmole (3S)-3-tert-butoxy-1-octyne in 1 ml toluene at 0° is added 0.42 ml of 2.4N n-butyl lithium solution. The resulting solution is stirred for ca. 5 minutes. To the reaction mixture is added 0.42 ml of 2.4M Me₂AlCl. The resulting solution is stirred at 0° for ¾ hour. To the above solution is added 291 mg (1 mmole) of silylacetal produced in part H in 1 ml of toluene. The reaction mixture is allowed to warm at ambient temperature then heated at 55° for 3 hours. To the cooled (0°) reaction mixture is added sufficient saturated Na₂SO₄ solution to decompose the aluminum complex, then solid Na₂SO₄ is added to consume the aqueous phase. The reaction mixture is diluted with ether, the salts filtered and washed, and the combined ether solutions are dried (MgSO₄). The solvent is evaporated to yield 450 mg of the crude (8R,9R,11S,12S,15S)-1,2,3,4,5-pentanor-9,11,15-trihydroxy-10,10-difluoro-13-prostyn-6-al 6,9 lactol, 6-t-butyldimethyl silyl ether, 15-t-butyl ether.

J. (8R,9R,11S,12S,15S)-1,2,3,4,5-pentanor-9,11,15-trihydroxy-10,10-difluoro-13-prostyn-6-al 6,9-lactol 15-t-butyl ether To an ice cooled solution of (ca. 1 mmole) silyl acetal produced in part I in 20 ml CH₃CN is added 0.8 ml of 48% HF. The reaction mixture is allowed to warm to ambient temperature and stir for 1½ hours. The reaction mixture is diluted with CH₂Cl₂ and powdered K₂CO₃ is added. The resulting solution is dried (MgSO₄) and the solvent is evaporated to yield the (8R,9R,11S,12S,15S)-1,2,3,4,5-pentanor-9,11,15-trihydroxy-10,10-difluoro-13-prostyn-6-al lactol 15-t-butyl ether.

K. (8R,9R,11S,12S,15S)-10,10-difluoro-13-dehydroprostaglandin $F_{2\alpha}$ 15-tert butyl ether, methyl ester To a solution of 5 mmole 4-carboxybutylidenetriphenylphosphorane sodium salt in 20 ml DMSO is added a solution of hemiacetal produced in part J in 2 ml DMSO. The reaction mixture is allowed to stir at ambient temperature for 1½ hours, then acidified to pH 2 with 0.2N HCl. The reaction mixture is extracted with ethyl acetate (4x). Combined ethyl acetate solutions are washed with saturated NaCl and dried (MgSO₄). Solvent is evaporated to yield crude product which is triturated with ether/ethyl acetate to remove the bulk of phosphine oxide. The crude product is dispersed in 25 ml of ether and esterified with CH₂N₂. Excess CH₂N₂ is quenched with acetic acid, the reaction mixture diluted with ether and washed with saturated KHCO₃, water, saturated NaCl and dried (MgSO₄). The solvent is evaporated to yield a crude product which is chromatographed on silica with pentane/Et₂O (2:1) to yield 216 mg of 10,10-difluoro-13-dehydro $PGF_{2\alpha}$ t-butyl ether methyl ester.

L. (8R,9R,11S,12S,15S)-10,10-difluoro-13-dehydroprostaglandin $F_{2\alpha}$ methyl ester To an ice cooled solution of 185 mg (0.4 mmole) the t-butyl ether produced in Park K and 50 μl anisole in 2 ml CH₂Cl₂ is added dropwise 1½ ml trifluoroacetic acid.

Reaction is allowed to warm to ambient temperature and stir for 80 minutes, then cooled with an ice bath, diluted with $CH_2Cl_2$ and ca. 10 ml saturated $KHCO_3$. The cooled reaction mixture is stirred until evolution of $CO_2$ ceases. The reaction mixture is again diluted with $CH_2Cl_2$ and the phases are separated. The aqueous phase is reextracted with $CH_2Cl_2$ and the combined $CH_2Cl_2$ phases are washed with saturated NaCl and dried ($MgSO_4$). Solvent is evaporated to yield 161 mg of crude 10,10-difluoro-13-dehydro $PGF_{2\alpha}$.

M.
(8R,9R,11S,12S,15S)-10,10-Difluoro-5-iodo-9-deoxy-6,9-epoxy-13-dehydroprostaglandin $F_{2\alpha}$ methyl ester To an ice cooled solution of ester produced in Part L (155 mg) in 30 ml ether is added 4 ml saturated $KHCO_3$ and 700 mg $I_2$. The reaction mixture is allowed to stir at ambient temperature for ca. 16 hours. The reaction mixture is diluted with ether and excess $I_2$ reduced with $Na_2S_2O_3$. The phases are separated and the aqueous phase is reextracted with ether. Combined ether phases are washed with saturated NaCl, dried ($MgSO_4$) and stripped of solvent to yield 250 mg of crude product. The iodoether is chromatographed on silica with pentane/ether (1:2) to yield 198 mg (95%) of title compound as a mixture of isomers.

N.
(8R,9R,11S,12S,15S)-10,10-Difluoro-13-dehydroprostacyclin methyl ester A solution of 190 mg (0.35 mmole) iodoether produced in Part M and 2 mmole DBU in 7 ml benzene is heated at 70°–85° (oil bath temperature) for ca. ½ hour. The reaction mixture is diluted with ether, washed with cold pH 5 buffer, saturated $KHCO_3$, saturated NaCl and dried ($MgSO_4$, $K_2CO_3$). The solvent is evaporated to yield 132 mg of crude product containing both desired 10,10-difluoro-13-dehydro $PGI_2$ methyl ester and the $\Delta^4$ isomer. The crude product is chromatographed on silica with hexane/ether (1:3) to yield 44 mg of difluoro, dehydro $PGI_2$ methyl ester.

EXAMPLE 2
[3aR-[2Z,3aα,4α(5S),5β,6aα]]-[6,6-Difluorohexahydro-5-hydroxy-4-(3-hydroxy-1-octynyl)-2H-cyclopenta[b]furan-2-ylidene]pentanoic acid, sodium salt or (8R,9R,11S,12S,15S)-10,10-Difluoro-13-dehydro prostacyclin sodium salt To an ice cooled solution of the ester of Example 1 in ¾ ml methanol is added ~1 ml of 1N NaOH. The reaction is allowed to stir for 2¾ hours at ambient temperature. The reaction mixture is diluted with ether, buffered to pH ca. 9 with $CO_2$ and solvent evaporated to yield a white solid which is dried in vacuo to yield 75 mg of the title salt embedded in $NaHCO_3$.

EXAMPLE 3
[3aS-[2Z,3aα,4α(5R*),5β,6aα]]-[6,6-Difluorohexahydro-5-hydroxy-4-(3-hydroxy-1-octynyl)-2H-cyclopenta[b]furan-2-ylidene]pentanoic acid (or 8S,9S,11R,12R,15R)-10,10-Difluoro-13-dehydro-prostacyclin methyl ester

A. 3-Allyl-1,1-difluoro-2,5-dihydroxycyclopentane

A stream of $FClO_3$, purified by bubbling successively through solutions of 2N NaOH and 5% $Na_2S_2O_3$, is bubbled via a gas dispersion tube into a mixture of 2.5 g (18 mmole) 5-allyl-cyclopentan-1,3-dione, and 3.8 g (38 mmole) of finely powdered $KHCO_3$ in 100 ml of ethanol. The temperature of the reaction medium is kept at 10°–25° with an ice bath. The reaction is vented through a water bubbler. Upon disappearance of starting diketone by TLC, flow of $FClO_3$ is stopped and the solution is purged of $FClO_3$ with $N_2$. A solution of KOH in 95% ethanol is used to detect presence of $FClO_3$ in effluent from the reaction flask. The reaction mixture is then cooled to $-20°$ with dry ice/$CCl_4$ and 0.7 g (18 mmole) of $NaBH_4$ is added in three portions. Temperature of the reaction medium is kept below $-15°$ C. After completion of addition, the reaction mixture is stirred at $-20°$ for ½ hour then quenched with solid $NH_4Cl$. The ethanol is removed on a rotary evaporator and the residue is digested with ethyl acetate. The combined ethyl acetate solutions are washed with saturated NaCl and dried ($MgSO_4$). The solvent is evaporated to give a quantitative yield of crude 3-allyl-1,1-difluoro-2,5-dihydroxycyclopentane as a mixture of all possible isomers. A sample of the all cis isomer is obtained by chromatography and characterized spectroscopically. $R_f=0.45$ [silica, benzene/EtOAc (2:1)].

B. 3,3-Difluoro-2,4-dihydroxycyclopentane-1-acetic acid 2,2' lactone

A stream of ozone is passed into a solution of 5 g of the isomeric mixture of 3-allyl-1,1-difluoro-2,5-dihydroxycyclopentane in 300 ml of methanol at $-78°$ until ozone is detected in the effluent stream (aqueous KI solution). The excess ozone is blown out of the reaction mixture with nitrogen, the reaction mixture is warmed to ambient temperature and the solvent is evaporated to yield crude product. The crude ozonolysis product is dissolved in 25 ml of 88% $HCO_2H$ and ca. 6.5 ml of 30% $H_2O_2$ is added. The reaction mixture is gently heated (ca. 40°–70°) until a vigorous exotherm occurs. After the exotherm ceases, an additional 13 ml of 30% $H_2O_2$ is added and the reaction is heated at 70° for 10 hours. The solvent is evaporated, the residue is taken up in EtOAc, washed with saturated $KHCO_3$, saturated NaCl and dried ($MgSO_4$). The solvent is evaporated to yield ca. 1.8 g of 3,3-difluoro-2,4-dihydroxycyclopentane-1-acetic acid 2,2' lactone (40% yield from 5-allyl-cyclopentan-1,3-dione). The lactone is a mixture of hydroxyl epimers; the all cis isomer predominates 6:1. The dihydroxy acid is obtained by acidification of the $KHCO_3$ solution and extraction with ethyl acetate. The isomeric lactones are separated by chromatography and characterized spectroscopically.

C. 3,3-Difluoro-1,2-cis-2-hydroxycyclopent-4-ene-1-acetic acid 2,2' lactone

To a solution of 2.3 g (12.9 mmole) crude 3,3-difluoro-2,4-dihydroxycyclopentane-1-acetic acid 2,2' lactone (in 2 ml of pyridine and 120 ml $CH_2Cl_2$) cooled to $-20°$ is added dropwise a solution of 3.81 g (13.5 mmole) of trifluoromethanesulfonic anhydride in 10 of $CH_2Cl_2$. Upon completion of addition, reaction is allowed to warm to ambient temperature and stir for ½ hour. The reaction mixture is diluted with $Et_2O$ and pyridinium triflate is filtered off. The filtrate is washed with water, saturated NaCl and dried ($MgSO_4$). Solvent is evaporated to yield 3.4 g of brown solid. To an ice cooled solution of the crude triflate in ca. 100 ml of toluene is added 1.7 g (11 mmole) of 1,5-diaza[5,4,0-]bicycloundec-5-ene (DBU). The reaction mixture is heated at 40°–50° (oil bath temperature) for ½ hour. The cooled reaction mixture is poured into ice/ethyl acetate and the layers are separated. The ethyl acetate phase is washed with pH 5.5 acetate buffer, saturated NaCl and dried ($MgSO_4$). The solution is filtered through celite and evaporated to yield 1.1 g (72%) of 3,3-difluoro-1,2-cis-2-hydroxycyclopent-4-ene-1-acetic acid 2,2′ lactone.

D. (1S,2S) 3,3-Difluoro-2-hydroxy-cyclopent-4-ene-1-acetic acid Naphthylethylamine salt To a solution of 6.5 g (0.041 mole) of olefin lactone produced in Part C in 120 ml THF and 85 ml water is added 62 ml of 1N NaOH. The resulting solution is stirred at ambient temperature for 4 hours. The THF is stripped off on a rotary evaporator and ethyl acetate (100 ml) is added. The reaction mixture is acidified with saturated oxalic acid to pH 2. The layers are separated and the aqueous phase is reextracted (4x). The combined ethyl acetate extracts are washed with saturated NaCl and dried ($MgSO_4$). The drying agent is filtered off, the ethyl acetate solution is treated with 8 ml (8.48 g, 0.05 mole) of (S)(−)-1-naphthyl-1-ethylamine and allowed to stand overnight. The salt is collected, dissolved in 2 l. hot ethyl acetate and filtered through celite to remove oxalate salt. The solution is concentrated and crude salt is recrystallized from ethyl acetate (twice) to yield 4.9 g of title salt, m.p. 162°–163° C.; $[\alpha]_D(CH_3OH) = +44.1°$ (c=1.5).

E. (1R,2R,3S,5S) 4,4-Difluoro-2,5-dihydroxy-3-iodocyclopentane-1-acetic acid 2,2′ lactone To an ice cooled suspension of 0.91 g (2.6 mmole) of chiral salt produced in Part D in 200 ml ether is added dropwise 2.65 ml of 1N aqueous methanesulfonic acid. Upon completion of addition, sufficient solid $(NH_4)_2SO_4$ is added to consume the aqueous phase. The ether is decanted and the solids are washed with ether. The combined ethyl ether solutions are dried ($Na_2SO_4$) and evaporated to give a quantitative yield of chiral hydroxy acid as a viscous oil. The hydroxy acid is taken up in 35 ml of 0.1N KOH in methanol and the pH of the solution adjusted to ca. 8.5 with $CO_2$ and $KHCO_3$. To the solution of hydroxy-carboxylate is added 6.7 g (26 mmole) of $I_2$ and the resulting solution allowed to stir at ambient temperature in the dark for 40 hours. Excess $I_2$ is reduced with aqueous $Na_2S_2O_3$ and the solvent is evaporated to give a yellow residue. The residue is digested with ethyl acetate and the combined solutions are washed with saturated $Na_2SO_3$, saturated NaCl and dried ($MgSO_4$). Solvent is evaporated to give a quantitative yield of the title compound.

F. (1S,2S,4R,5R) 3,3-Difluoro-2-hydroxy-3,4-epoxycyclopentane-1-acetic acid 2,2′ lactone To a solution of 0.75 g (2.5 mmole) iodolactone produced in Part E in 8 ml THF is added 12 ml of 0.42N KOH. The reaction is stirred at ambient temperature for 3½ hours. At the end of this period TLC shows absence of starting lactone. The reaction mixture is acidified with $CO_2$ to pH 7, then to pH 3 with saturated oxalic acid solution. The THF is evaporated and the aqueous solution is saturated with NaCl and extracted with ethyl acetate (4x). Combined ethyl acetate solutions are dried ($Na_2SO_4$) and the solvent is evaporated to yield 430 mg of crude crystalline epoxy acid. The acid is dispersed in 5 ml $CH_2Cl_2$, cooled with an ice bath and treated dropwise with 0.35 ml (2.5 mmole) of trifluoroacetic anhydride. Upon stirring briefly the acid dissolves and the volatile components are evaporated to yield 410 mg of the title compound (88% yield from iodolactone of Part E). $[\alpha]_D(CHCl_3) = +102.9$ (c=0.10).

G. (1S,2S,4R,5R) 3,3-Difluoro-2-hydroxy-4,5-epoxycyclopentane-1-acetaldehyde 2,2′-lactol To a suspension of 403 mg (2.28 mmole) of epoxy lactone produced in Part F in 10 ml of toluene at −78° is added dropwise 14 ml of a 1.5M solution of diisobutylaluminum hydride in toluene. Reaction is allowed to stir at −78° until all of the starting lactone is dissolved (~3-4 hours). The reaction is quenched with 1 equivalent of acetic acid in ether and the dry ice bath is removed. The aluminum complex is quenched with 3N HCl, saturated with NaCl. The reaction mixture is diluted with ethyl acetate and the phases separated. The aqueous phase is extracted with ethyl acetate (4x). The combined organic phase is washed with saturated $KHCO_3$, saturated NaCl and dried ($MgSO_4$). The solvent is evaporated to yield 385 mg of the title compound.

H. (1S,2S,4R,5R) 3,3-Difluoro-2-hydroxy-4,5-epoxycyclopentane-1-acetaldehyde 2,2′ lactol t-butyldimethyl silyl ether To a solution of 384 mg (2.16 mmole) of hemiacetal of part G and 375 mg (2.5 mmole) of tert-butyl dimethylsilyl chloride in 7 ml of DMF is added 303 mg of triethylamine and 60 mg (½ mmole) of 4-(N,N-dimethylamino)-pyridine. The resulting solution is stirred at ambient temperature overnight. The reaction is poured into ether/water and the layers are separated. The ether phase is washed with saturated $KHCO_3$, saturated NaCl and dried ($MgSO_4$). Solvent is evaporated to yield the title compound. The crude product is chromatographed on silica with hexane/ethyl acetate to yield 390 mg of the silyl acetal.

I. (8S,9S,11R,12R,15R)-1,2,3,4,5-Pentanor-9,11,15-trihydroxy-10,10-difluoro-13-prostyn-6-al 6,9-lactol 6-t-butyldimethyl silyl ether, 15-t-butyl ether To a solution of 1 mmole (3R)-3-tertbutoxy-1-octyne in 1 ml toluene at 0° is added 0.42 ml of 2.4N n-butyl lithium solution. The resulting solution is stirred for ca. 5 minutes. To the reaction mixture is added 0.42 ml of 2.4M $Me_2AlCl$. The resulting solution is stirred at 0° for ¾ hour. To the above solution is added 291 mg (1 mmole) of silylacetal produced in part H in 1 ml of toluene. The reaction mixture is allowed to warm at ambient temperature then heated at 55° for 3 hours. To the cooled (0°) reaction mixture is added sufficient saturated $Na_2SO_4$ solution to decompose the aluminum complex, then solid $Na_2SO_4$ is added to consume the aqueous phase. The reaction mixture is diluted with ether, the salts filtered and washed, and the combined ether solutions are dried ($MgSO_4$). The solvent is evaporated to yield 450 mg of the crude title compound.

J.
(8S,9S,11R,12R,15R)-1,2,3,4,5-Pentanor-9,11,15-trihydroxy-10,10-difluoro-13-prostyn-6-al 6,9-lactol 15-t-butyl ether To an ice cooled solution of (ca. 1 mmole) silyl acetal produced in part I in 20 ml $CH_3Cn$ is added 0.8 ml of 48% HF. The reaction mixture is allowed to warm to ambient temperature and stir for 1½ hours. The reaction mixture is diluted with $CH_2Cl_2$ and powdered $K_2CO_3$ is added. The resulting solution is dried ($MgSO_4$) and the solvent is evaporated to yield the (340 mg crude) title compound.

K.
(8S,9S,11R,12R,15R)-10,10-difluoro-13-dehydro-prostaglandin $F_{2\alpha}$ 15-t-butyl ester, methyl ester To a solution of 5 mmole of 4-carboxybutylidenetriphenylphosphorane sodium salt in 20 ml DMSO is added a solution of hemiacetal produced in part J in 2 ml DMSO. The reaction mixture is allowed to stir at ambient temperature for 1½ hours, then acidified to pH 2 with 0.2N HCl. The reaction mixture is extracted with ethyl acetate (4x). Combined ethyl acetate solutions are washed with saturated NaCl and dried ($MgSO_4$). Solvent is evaporated to yield crude product which is triturated with ether/ethyl acetate to remove the bulk of phosphine oxide. The crude product is dispersed in 25 ml of ether and esterified with $CH_2N_2$. Excess $CH_2N_2$ is quenched with acetic acid, the reaction mixture diluted with ether and washed with saturated $KHCO_3$, water, saturated NaCl and dried ($MgSO_4$). The solvent is evaorated to yield a crude product which is chromatographed on silica with pentane/$Et_2O$ (2:1) to yield 216 mg of 10,10-difluoro-13-dehydro $PGE_{2\alpha}$-t-butyl ether methyl ester.

L.
(8S,9S,11R,12R,15R)-10,10-Difluoro-13-dehydroprostaglandin $F_{2\alpha}$ methyl ester To an ice cooled solution of 185 mg (0.4 mmole) the t-butyl ether produced in Part K and 50 μl anisole in 2 ml $CH_2Cl_2$ is added dropwise 1½ ml trifluoroacetic acid. Reaction is allowed to warm to ambient temperature and stir for 80 minutes, then cooled with an ice bath, diluted with $CH_2Cl_2$ and ca. 10 ml saturated $KHCO_3$. The cooled reaction mixture is stirred until evolution of $CO_2$ ceases. The reaction mixture is again diluted with $CH_2Cl_2$ and the phases are separated. The aqueous phase is reextracted with $CH_2Cl_2$ and the combined $CH_2Cl_2$ phases are washed with saturated NaCl and dried ($MgSO_4$). Solvent is evaporated to yield 161 mg of crude 10,10-difluoro-13-dehydro $PGF_{2\alpha}$ methyl ester.

M.
(8S,9S,11R,12R,15R)-10,10-Difluoro-5-iodo-9-deoxy-6,9-epoxy-13-dehydroprostaglandin $F_{2\alpha}$ methyl ester To an ice cooled solution of ester produced in Part L (155 mg) in 30 ml ether is added 4 ml saturated $KHCO_3$ and 700 mg $I_2$. The reaction mixture is allowed to stir at ambient temperature for ca. 16 hours. The reaction mixture is diluted with ether and excess $I_2$ reduced with $Na_2S_2O_3$. The phases are separated and the aqueous phase is reextracted with ether. Combined ether phases are washed with saturated NaCl, dried ($MgSO_4$) and stripped of solvent to yield 250 mg of crude product. The iodoether crude product is chromatographed on silica with pentane/ether (1:2) to yield 198 mg (95%) of title compound as a mixture of isomers.

N.
(8S,9S,11R,12R,15R)-10,10-Difluoro-13-dehydroprostacyclin methyl ester A solution of 190 mg (0.35 mmole) iodoether produced in Part M and 2 mmole DBU in 7 ml benzene is heated at 70°–85° (oil bath temperature) for ca. ½ hour. The reaction mixture is diluted with ether, washed with cold pH 5 buffer, saturated $KHCO_3$, saturated NaCl and dried ($MgSO_4$, $K_2CO_3$). The solvnt is evaporated to yield 132 mg of crude product containing both desired 10,10-difluoro-13-dehydro $PGI_2$ methyl ester and the $\Delta^4$ isomer. The crude product is chromatographed on silica with hexane/ether (1:3) to yield 44 mg of difluoro, dehydro $PGI_2$ methyl ester.

EXAMPLE 4
[3aS-[2Z,3aα,4α(5R*),5β,6aα]]-[6,6-Difluorohexahydro-5-hydroxy-4-(3-hydroxy-1-octynyl)-2H-cyclopenta[b]furan-2-ylidene]pentanoic acid, sodium salt (or 8S,9S,11R,12R,15R) 10,10-Difluoro-13-dehydro prostacyclin sodium salt)

To an ice cooled solution of the ester of Example 3 in ¾ ml methanol is added ~1 ml of 1N NaOH. The reaction is allowed to stir for 2¾ hours at ambient temperature. The reaction mixture is diluted with ether, buffered to pH ca. 9 with $CO_2$ and solvent evaporated to yield a white solid which is dried in vacuo to yield 75 mg of the title salt embedded in $NaHCO_3$.

EXAMPLE 5
(8R,9R,11S,12S,15S)-10,10-Difluoroprostacyclin methyl ester

A.
(8R,9R,11S,12S,15S)-1,2,3,4,5-Pentanor-9,11,15-trihydroxy-10,10-difluoro-13-prosten-6-al 6,9-lactol 6-t-butyldimethyl silyl 15-t-butyl ester To a suspension of $LiAlH_4$ in THF (2.5 ml) at −40° is added within 2 minutes a solution of the silyl acetal produced in part I of Example 1 in THF (2.0 ml) under $N_2$ and the reaction mixture stirred at this temperature for 3 hours. The reaction is quenched by the dropwise addition of saturated NaK tartrate (1.5 ml). The suspension is extracted with EtOAc, dried ($Na_2SO_4$) and evaporated to dryness. The drude reaction product is purified by tlc. [$CHCl_3$:MeOH 9:1] to give the pure title compound.

B. (8R,9R,11S,12S,15S)-1,2,3,4,5-Pentanor 9,11,15-trihydroxy-10,10-difluoro-13-prosten-6-al 6,9-lactol 15-t-butyl ester To an ice cooled solution of (ca. 1 mmole) silyl acetal produced in part A in 20 ml $CH_3CN$ is added 0.8 ml of 48% HF. The reaction mixture is allowed to warm to ambient temperature and stir for 1½ hours. The reaction mixture is diluted with $CH_2Cl_2$ and powdered $K_2CO_3$ is added. The resulting solution is dried ($MgSO_4$) and the solvent is evaporated to yield the hemiacetal (340 mg crude).

C. (8R,9R,11S,12S,15S)-10,10-Difluoro-prostaglandin $F_{2\alpha}$ methyl ester 15-t-butyl ether To a solution of 5 mmole 4-carboxybutylidenetriphenylphosphorane sodium salt in 20 ml DMSO is added a solution of hemiacetal produced in part C in 2 ml DMSO. The reaction mixture is allowed to stir at ambient temperature for 1½ hours then acidified to pH 2 with 0.2N HCl. The reaction mixture is extracted with ethyl acetate (4x). Combined ethyl acetate solutions are washed with saturated NaCl and dried (MgSO$_4$). Solvent is evaporated to yield crude product which the is triturated with ether/ethyl acetate to remove bulk of phosphine oxide. The crude product is dispersed in 25 ml of ether and esterified with CH$_2$N$_2$. Excess CH$_2$N$_2$ is quenched with acetic acid, the reaction mixture diluted with ether and washed with saturated KHCO$_3$, water, saturated NaCl and dried (MgSO$_4$). The solvent is evaporated to yield a crude product which is chromatographed on silica with pentane/Et$_2$O (2:1) to yield 216 mg of difluoro, PGF$_{2\alpha}$ t-butyl ether methyl ester.

D. (8R,9R,11S,12S,15S)-10,10-Difluoroprostaglandin F$_{2\alpha}$ methyl ester

To an ice cooled solution of 185 mg (0.4 mmole) the t-butyl ether produced in Part C and 50 μl anisole in 2 ml CH$_2$Cl$_2$ is added dropwise 1½ ml TFA. Reaction is allowed to warm to ambient temperature and stir for 80 minutes, then cooled with an ice bath, diluted with CH$_2$Cl$_2$ and ca. 10 ml saturated KHCO$_3$. Cooled reaction is stirred until evolution of CO$_2$ ceases. The reaction mixture is again diluted with CH$_2$Cl$_2$ and the phases are separated. The aqueous phase is reextracted with CH$_2$Cl$_2$ and the combined CH$_2$Cl$_2$ phases are washed with saturated NaCl and dried (MgSO$_4$). Solvent is evaporated to yield 161 mg of crude difluoro, PGF$_{2\alpha}$ methyl ester.

E. (8R,9R,11S,12S,15S)-10,10-Difluoro-5-iodo-9-deoxy-6,9-epoxy-prostaglandin F$_{2\alpha}$ methyl ester To an ice cooled solution of ester produced in Part E (155 mg) in 30 ml ether is added 4 ml saturated KHCO$_3$ and 700 mg I$_2$. The reaction mixture is allowed to stir at ambient temperature for ca. 16 hours. The reaction mixture is diluted with ether and excess I$_2$ reduced with Na$_2$S$_2$O$_3$. The phases are separated and the aqueous phase is reextracted with ether. Combined ether phases are washed with saturated NaCl, dried (MgSO$_4$) and stripped of solvent to yield 250 mg of crude product. The iodoether crude product is chromatographed on silica with pentane/ether (1:2) to yield 198 mg (95%) of title compound as a mixture of isomers.

F. (8R,9R,11S,12S,15S)-10,10-Dilfluoroprostacyclin methyl ester

A solution of 190 mg (0.35 mmole) iodoether produced in Part E and 2 mmole DBU in 7 ml benzene is heated at 70°-85° (oil bath temperature) for ca. ½ hour. The reaction mixture is diluted with ether, washed with cold pH 5 buffer, saturated KHCO$_3$, saturated NaCl and dried (MgSO$_4$, K$_2$CO$_3$). The solvent is evaporated to yield 132 mg of crude product containing both desired difluoro, PGI$_2$ methyl ester and the Δ$^4$ isomer. The crude product is chromatographed in silica with hexane/ether (1:3) to yield 44 mg of difluoro, methyl ester.

EXAMPLE 6

[3αR-[2Z,3aα,4α(4E,5S*),5β,6aα]]-[6,6-Difluorohexahydro-5-hydroxy-4-(3-hydroxy-1-octenyl)-2H-cyclopenta[b]furan-2-ylidene]pentanoic acid sodium salt (or (8R,9R,11S,12S,15S)-10,10-Difluoroprostacyclin sodium salt))

To an ice cooled solution of the ester of Example 5 in ¾ ml methanol is added ~1 ml of 1N NaOH. The reaction is allowed to stir for 2¾ hours at ambient temperature. The reaction mixture is diluted with ether, buffered to pH ca. 9 with CO$_2$ and solvent evaporated to yield a white solid which is dried in vacuo to yield 75 mg of the title salt embedded in NaHCO$_3$.

EXAMPLE 7

3,3-Difluoro-1,2-cis-2-hydroxy-cyclopent-4-ene-1-acetic acid 2,2' lactone

A. 3,3-Difluoro-2,4-dihydroxy-cyclopentane-1-acetic acid methyl ester 3,3-Difluoro-2,4-dihydroxy-cyclopentane-1-acetic acid (obtained from acidification of KHCO$_3$ extract of ozonolysis reaction mixture in Example 1, part B) is stirred overnight in methanolic HCl. The methanol is evaporated and the residue is digested with ethyl acetate. The ethyl acetate solution is washed with saturated KHCO$_3$, saturated NaCl and dried (MgSO$_4$). The solvent is evaporated to yield the methyl ester A.

B. 3,3-Difluoro-1,2-cis-2-hydroxycyclopent-4-ene-1-acetic acid 2,2' lactone

To a solution of 5.3 g (25 mmoles) of methyl 3,3-difluoro-2,4-dihydroxycyclopentylacetate from part A, 8 ml pyridine in CH$_2$Cl$_2$ (100 ml) at 0° is added 15.5 g (55 mmole) of trifluoromethanesulfonic anhydride. Upon completion of addition, the reaction mixture is allowed to warm to ambient temperature and stir for ½ hour. The reaction mixture is diluted with ether and the pyridinium triflate is filtered off. The solvent is evaporated to yield the crude triflate which is heated at 40°-50° in benzene (10 ml) with 3.2 ml of DBU. The cooled reaction mixture is poured into ice/ethyl acetate and the layers are separated. The organic phase is washed with pH 5.5 buffer, saturated NaCl and dried (MgSO$_4$). The solution is filtered through celite and evaporated to yield olefin ester. The title compound in THF (20 ml) is treated with 36.6 ml of 1N KOH solution. The reaction mixture is stirred at room temperature for 1 hour then acidified to pH 7 with CO$_2$ and then to pH 2 with oxalic acid solution. The THF is evaporated in vacuo and the residue extracted with CH$_2$Cl$_2$. The CH$_2$Cl$_2$ extracts are treated with 1.5 g of trifluoroacetic anhydride and evaporated to yield 2.0 g of the title unsaturated lactone (50% overall yield) which may be employed in the examples and synthesis described above.

What is claimed is:

1. A method for preparing an unsaturated difluoro lactone compound of the structure

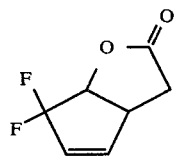

and stereoisomers thereof, which includes the steps of reacting 3,3-difluoro-2,4-dihydroxy-cyclopentaneacetic acid with alkanolic hydrochloric acid to form the corresponding alkyl ester, reacting the alkyl ester with trifluoromethanesulfonic anhydride to form the triflate of the structure

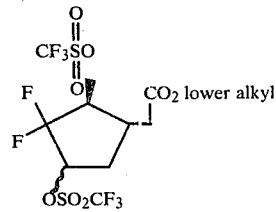

reacting the triflate with diazabicyclo[5,4,0]undec-5-ene to form the olefin ester treating the olefin ester with an alkali metal hydroxide, acidifying same, and then reacting same with trifluoroacetic anhydride to form the difluoro lactone.

* * * * *

UNITED STATES PATENT AND TRADEMARK OFFICE
CERTIFICATE OF CORRECTION

PATENT NO. : 4,463,183  
DATED : July 31, 1984  
INVENTOR(S) : Martin F. Haslanger Page 1 of 3

It is certified that error appears in the above—identified patent and that said Letters Patent is hereby corrected as shown below:

In the abstract, the first three structures should read

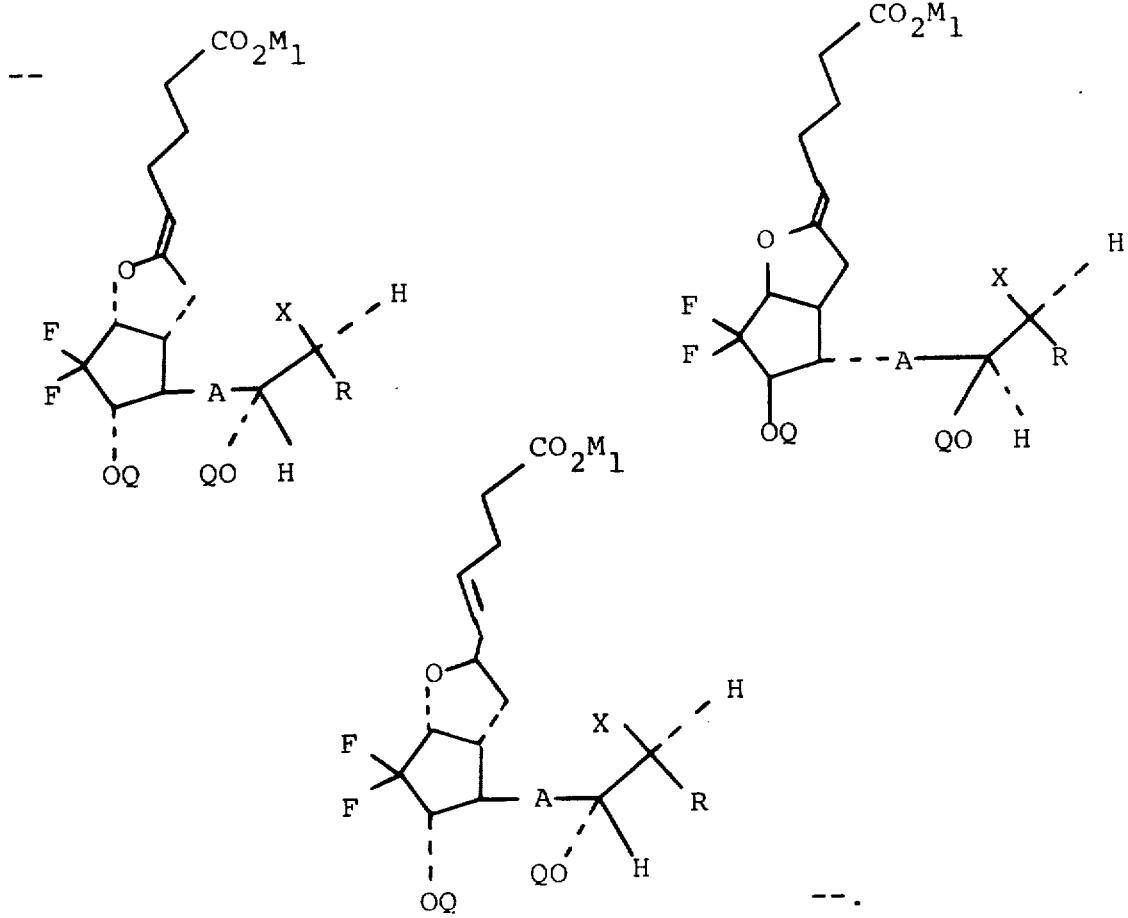

--.

UNITED STATES PATENT AND TRADEMARK OFFICE
CERTIFICATE OF CORRECTION

PATENT NO. : 4,463,183
DATED : July 31, 1984
INVENTOR(S) : Martin F. Haslanger

It is certified that error appears in the above—identified patent and that said Letters Patent is hereby corrected as shown below:

Column 7, line 20, structure XI' should read

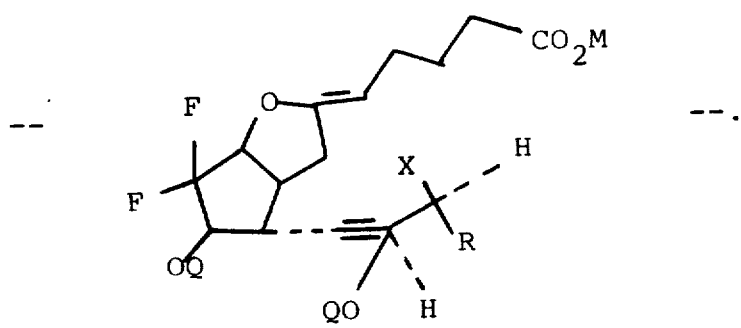

Column 7, line 33, structure XIA' should read

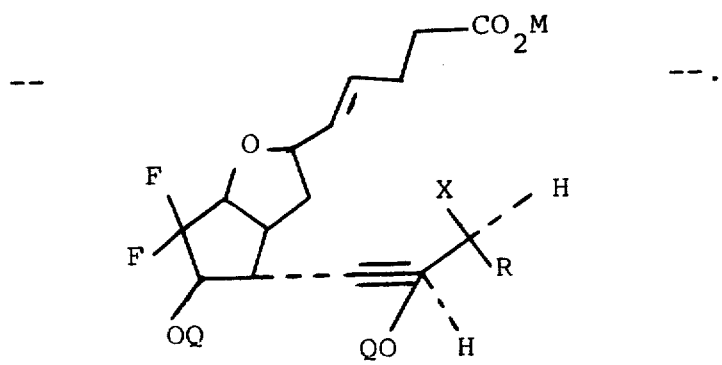

UNITED STATES PATENT AND TRADEMARK OFFICE
CERTIFICATE OF CORRECTION

PATENT NO. : 4,463,183
DATED : July 31, 1984
INVENTOR(S) : Martin F. Haslanger

It is certified that error appears in the above—identified patent and that said Letters Patent is hereby corrected as shown below:

Column 8, line 10, structure IV' should read

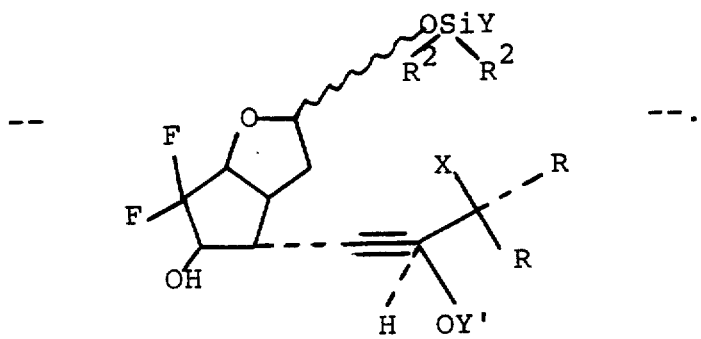

Column 13, line 20, "FCLO$_3$" should read --FClO$_3$--.
Column 23, line 7, "CH$_3$Cn" should read --CH$_3$CN--.
Column 24, line 12, "solvnt" should read --solvent--.

Signed and Sealed this

Eighteenth Day of December 1984

[SEAL]

Attest:

GERALD J. MOSSINGHOFF

Attesting Officer   Commissioner of Patents and Trademarks